(12) United States Patent
Arudra

(10) Patent No.: US 10,843,181 B2
(45) Date of Patent: Nov. 24, 2020

(54) METHOD OF MAKING A FLUORIDE FUNCTIONALIZED ZEOLITE CATALYST AND METHOD OF USE

(71) Applicant: King Fahd University of Petroleum and Minerals, Dhahran (SA)

(72) Inventor: Palani Arudra, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 15/994,293

(22) Filed: May 31, 2018

(65) Prior Publication Data
US 2019/0366321 A1 Dec. 5, 2019

(51) Int. Cl.
| | | |
|---|---|---|
| B01J 37/26 | (2006.01) | |
| B01J 29/40 | (2006.01) | |
| C07C 4/06 | (2006.01) | |
| C07C 11/06 | (2006.01) | |
| C07C 11/08 | (2006.01) | |
| B01J 35/10 | (2006.01) | |
| C07C 11/04 | (2006.01) | |

(52) U.S. Cl.
CPC ............... *B01J 37/26* (2013.01); *B01J 29/40* (2013.01); *C07C 4/06* (2013.01); *B01J 35/1019* (2013.01); *B01J 2229/26* (2013.01); *C07C 11/04* (2013.01); *C07C 11/06* (2013.01); *C07C 11/08* (2013.01); *C07C 2529/40* (2013.01)

(58) Field of Classification Search
CPC .............. B01J 37/26; B01J 29/40; C07C 4/06
USPC ......................................................... 502/60
See application file for complete search history.

(56) References Cited

U.S. PATENT DOCUMENTS

| | | | | |
|---|---|---|---|---|
| 2,477,695 A | * | 8/1949 | Kimberlin, Jr. ........ | C01B 33/143 106/287.17 |
| 4,073,865 A | * | 2/1978 | Flanigen ................ | B01D 53/02 423/335 |
| 4,324,698 A | | 4/1982 | Lewis et al. | |
| 5,772,980 A | * | 6/1998 | Sul .......................... | C01B 39/40 423/705 |

(Continued)

FOREIGN PATENT DOCUMENTS

| | | |
|---|---|---|
| CN | 1093510 C | 10/2002 |
| CN | 101837990 B | 8/2012 |

(Continued)

OTHER PUBLICATIONS

Comparative Study of Nano-ZSM-5 Catalysts Synthesized in OH- and F-media Zhengxing Qin et al. Adv. Funct. Mater. V24, pp. 257-264 (Year: 2014).*

(Continued)

*Primary Examiner* — Douglas B Call
(74) *Attorney, Agent, or Firm* — Oblon, McClelland, Maier & Neustadt, L.L.P.

(57) ABSTRACT

A method for producing a fluoride functionalized zeolite catalyst is described, having a F/Si molar ratio of 0.1:1-3:1. The method involves mixing a fluoride salt with zeolite components to form a gel, which is then hydrothermally treated and calcined. The fluoride functionalized zeolite catalyst may be used for cracking an olefin stream into ethylene, propylene, and butylene, with high selectivity towards propylene. The fluoride functionalized zeolite catalyst may be used for 50 or more hours with a stable conversion rate and low coke formation.

10 Claims, 3 Drawing Sheets

(56) References Cited

U.S. PATENT DOCUMENTS

2006/0052649 A1* 3/2006 Kemnitz .................. B01J 27/12
570/166

FOREIGN PATENT DOCUMENTS

| CN | 102745717 A | 10/2012 |
|---|---|---|
| KR | 10-2011-0129179 | 12/2011 |

OTHER PUBLICATIONS

Acidity Adjustment of HZSM-5 Zeolites by Dealumination and Realumination with Steaming and Citric Acid treatments. Yu Fan et al. J. Phys. Chem. B: vol. 110, pp. 15411-15416 (Year: 2006).*

Machine translation of CN101269340, pp. 1-6, downloaded Sep. 20, 2019 (Year: 2008).*

Microporous and Mesoporous Materials, V 74, pp. 171-178 (Year: 2004).*

Ting Xu, et al., "Fluoride-treated H-ZSM-5 as a highly selective and stable catalyst for the production of propylene from methyl halides", Journal of Catalysis, vol. 295, Nov. 2012, pp. 232-241.

Zhicheng Tang, et al., "Butene catalytic cracking to ethylene and propylene on fluorinated ZSM-5-based catalyst", Reaction Kinetics, Mechanisms and Catalysis, vol. 108, Issue 1, Feb. 2013, pp. 231-239.

Xiang Feng, et al., "Highly Effective F-Modified HZSM-5 Catalysts for the Cracking of Naphtha to Produce Light Olefins", Energy Fuels, vol. 24, No. 8, 2010, pp. 4111-4115.

Pushparaj Hemalatha, et al., "Effects of crystallinity of ZSM-5 zeolite on para-selective tert-butylation of ethylbenzene", Chinese Journal of Catalysis, vol. 34, Feb. 20, 2013, pp. 294-304.

Jiangyin Lu, et al., "Effects of Calcination Temperature on the Acidity and Catalytic Performances of HZSM-5 Zeolite Catalysts for the Catalytic Cracking of n-Butane", Journal of Natural Gas Chemistry, vol. 14, No. 4, 2005, pp. 213-220.

Yasuhide Gao, et al., "Influence on Fluorine on the Catalytic Performance of Ti-Beta Zeolite", J. Phys. Chem. B, vol. 108, No. 14, 2004, pp. 4242-4244.

* cited by examiner

METHOD OF MAKING A FLUORIDE FUNCTIONALIZED ZEOLITE CATALYST AND METHOD OF USE

BACKGROUND OF THE INVENTION

Technical Field

The present invention relates to a method of making a fluoride functionalized zeolite catalyst and a method of using a fluoride functionalized zeolite catalyst to catalytically crack an olefin stream into lighter hydrocarbon products.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Propylene and ethylene are crucial components in the petrochemical industry to produce many chemical intermediates and polymers such as polypropylene, oxo alcohols, propylene oxide, cumene, methyl methacrylate, phenol, acrylic acid, isopropyl alcohol, acrylonitrile, oligomers, and other miscellaneous intermediates. The main source of propylene production in the petrochemical industry is as a byproduct from fluid catalytic cracking (FCC) units or as the product from processing ethane and heavier feedstocks in steam crackers. The amount of propylene coproduced in a steam cracker depends mostly on the nature of the feedstock. However, with the recent sharp decline in oil prices, the cost advantage of ethane cracking has diminished, and cracker operators are likely to crack heavier feeds and produce more propylene. This scenario may be changed once again with an increase in oil prices. Based on the ethylene and propylene market price fluctuations, the P/E (propylene/ethylene) ratio plays an important factor in catalytic cracking of olefins. Commercially, Olefin Cracking Process (UOP-ATOFINA), Propylur (Lurgi), PCC process (Exxon-Mobil), SUPER-FLEX® (Lyondell/Kellogg) and Mobil's Olefin Interconversion Process (MOI) are available for production of lower olefins such as ethylene and propylene using $C_4$-$C_5$ streams. Cracking of $C_4$-$C_6$ alkenes appears to be a promising route for the production of propylene and ethylene.

Nawaz et al. showed the role of bulk topology/structure of SAPO-34 catalysts using 1-hexene catalytic cracking. However, the catalyst deactivation rate was much faster when compared to ZSM-5 catalysts. See Nawaz, Z. et al. *Chin J Catal,* 30 (2009) 1049-1057—incorporated herein by reference in its entirety Buchanan et al. showed higher propylene selectivity (83%) with lower 1-hexene conversion (66%) using ZSM-5 with a $Si/Al_2$ ratio of 650 at 510° C. and with a 10 Torr partial pressure. See Buchanan et al. *J. Catalysis,* 158 (1996) 279-287—incorporated herein by reference in its entirety.

Koyama et al. studied the effect of pore volume on propylene selectivity in 1-hexene cracking using ZSM-22 as catalyst. The selectivity for propylene gradually decreased from 93% to 80% with increasing conversion of 1-hexene from about 1 to 80%. However, the stability of the catalyst was not reported. See Koyama et al. *Phys. Chem. Chem. Phys.,* 12 (2010) 2541-2554—incorporated herein by reference in its entirety.

Yuxiang Liu et al. showed the role of fluoride ion in the synthesis of SAPO-11. The fluoride ion inhibits coke deposition by suppressing condensation reactions. See Liu, Yuxiang et al. *Microporous and Mesoporous Materials* 198 (2014) 230-235—incorporated herein by reference in its entirety.

The foregoing discussions show that there has been no report available in effect of fluoride ion in synthesis of ZSM-5 catalyst to enhance the catalytic cracking of higher olefins to propylene and ethylene.

In view of the foregoing, one objective of the present invention is to provide a method of making a fluoride functionalized zeolite catalyst, and a method of using a fluoride functionalized zeolite catalyst for cracking a $C_4$-$C_6$ olefin into ethylene, propylene, and/or butylene.

BRIEF SUMMARY OF THE INVENTION

According to a first aspect, the present disclosure relates to a method for producing a fluoride functionalized zeolite catalyst. The method involves the step of mixing a structure directing agent, an inorganic fluoride salt, an aluminum salt, a silicating agent, and water to form a gel, where the gel has a F to Si molar ratio of 0.1:1.0-3.0:1.0. The method involves the step of heating the gel at 180-250° C. for 12-72 h to produce a crystallized product, and calcining the crystallized product in air at 600-850° C. for 3-12 h to produce the fluoride functionalized zeolite catalyst.

In one embodiment, the structure directing agent is a quaternary ammonium salt with a chemical formula $N(C_nH_{3n})_4^+X^-$. X is a halide ion or a hydroxide, and n is an integer from 1 to 5.

In one embodiment, the inorganic fluoride salt is ammonium fluoride.

In one embodiment, the gel and the fluoride functionalized zeolite catalyst are substantially free of phosphorous and sodium.

In one embodiment, the aluminum salt is aluminum nitrate or aluminum sulfate.

In one embodiment, the fluoride functionalized zeolite catalyst has a Si to Al molar ratio of 500:1-2,000:1.

In one embodiment, the fluoride functionalized zeolite catalyst has an average crystal size of 0.1-50 µm.

In one embodiment, the fluoride functionalized zeolite catalyst has a total acidity of 0.017-0.020 mmol/g as defined by $NH_3$-TPD.

In one embodiment, the silicating agent is at least one selected from the group consisting of tetraethylorthosilicate, tetramethylorthosilicate, silica, and polydimethylsiloxane.

In one embodiment, the fluoride functionalized zeolite catalyst is a ZSM-5 type zeolite.

In one embodiment, the fluoride functionalized zeolite catalyst has a surface area of 330-400 $m^2/g$.

According to a second aspect, the present disclosure relates to a fluoride functionalized zeolite catalyst produced by the method of the first aspect.

According to a third aspect, the present disclosure relates to a method of using a fluoride functionalized zeolite catalyst to convert a $C_4$-$C_6$ olefin into ethylene, propylene, and/or butylene. The method involves contacting a gas stream comprising the $C_4$-$C_6$ olefin with the fluoride functionalized zeolite catalyst at a temperature of 400-700° C. to produce ethylene, propylene, and/or butylene. Here, the fluoride functionalized zeolite catalyst has a F to Si molar ratio of 0.1:1.0-3.0:1.0 and an average particle size of 0.1-5.0 mm. Additionally, at least 75 mol % of the $C_4$-$C_6$ olefin present is converted to ethylene, propylene, and/or butylene.

In one embodiment, at least 85 mol % of the $C_4$-$C_6$ olefin present is converted to ethylene, propylene, and/or butylene.

In one embodiment, the $C_4$-$C_6$ olefin is 1-hexene, and a mole percentage of propylene produced with respect to moles 1-hexene consumed is 60-85%.

In one embodiment, the $C_4$-$C_6$ olefin is 1-hexene, and over a reaction period of 24-72 hours, at least 85 mol % of the 1-hexene present is converted to ethylene, propylene, and/or butylene, and a mole percentage of propylene produced with respect to moles 1-hexene converted is 60-85%.

In one embodiment, the $C_4$-$C_6$ olefin is present in the gas stream at a partial pressure of 20-500 kPa.

In one embodiment, the gas stream further comprises an inert carrier gas.

In one embodiment, the fluoride functionalized zeolite catalyst is substantially free of phosphorous and sodium.

In one embodiment, the $C_4$-$C_6$ olefin is fed to a fixed bed reactor at a flow rate of 5-20 mL/h per g fluoride functionalized zeolite catalyst.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
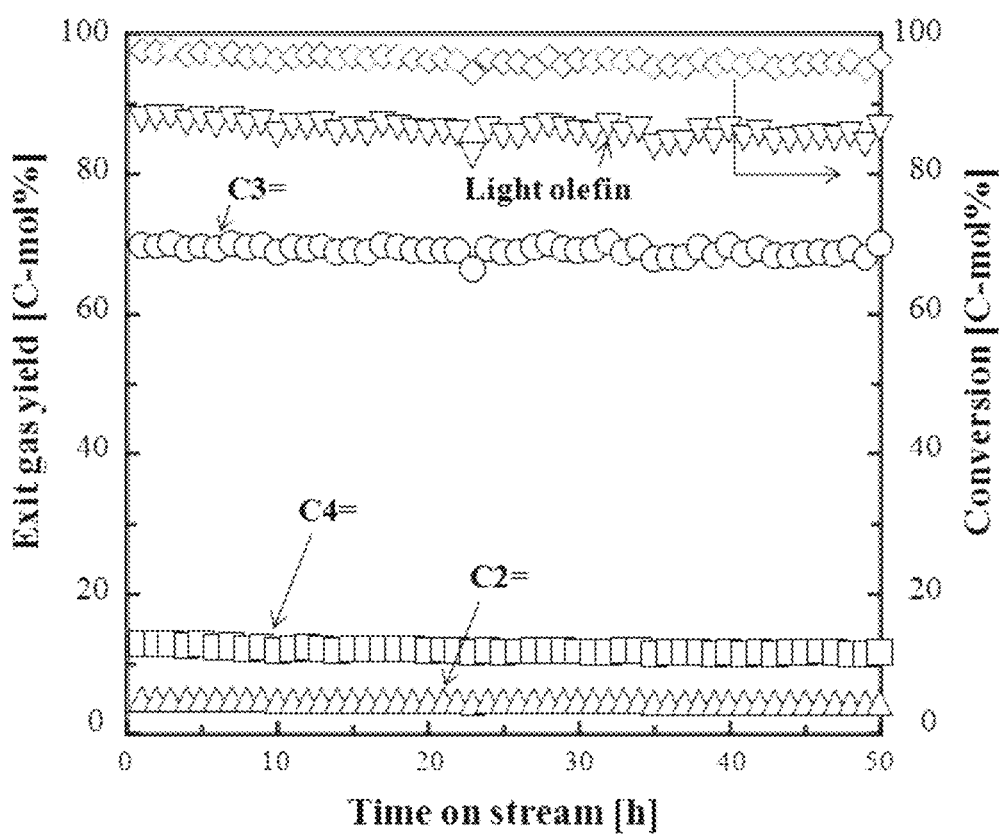
FIG. 1 is a graph showing an exit gas yield and reactant conversion for a fluoride functionalized zeolite catalyst having a F/Si ratio=2 over a 1-hexene stream for 50 hours.
Figure 2:
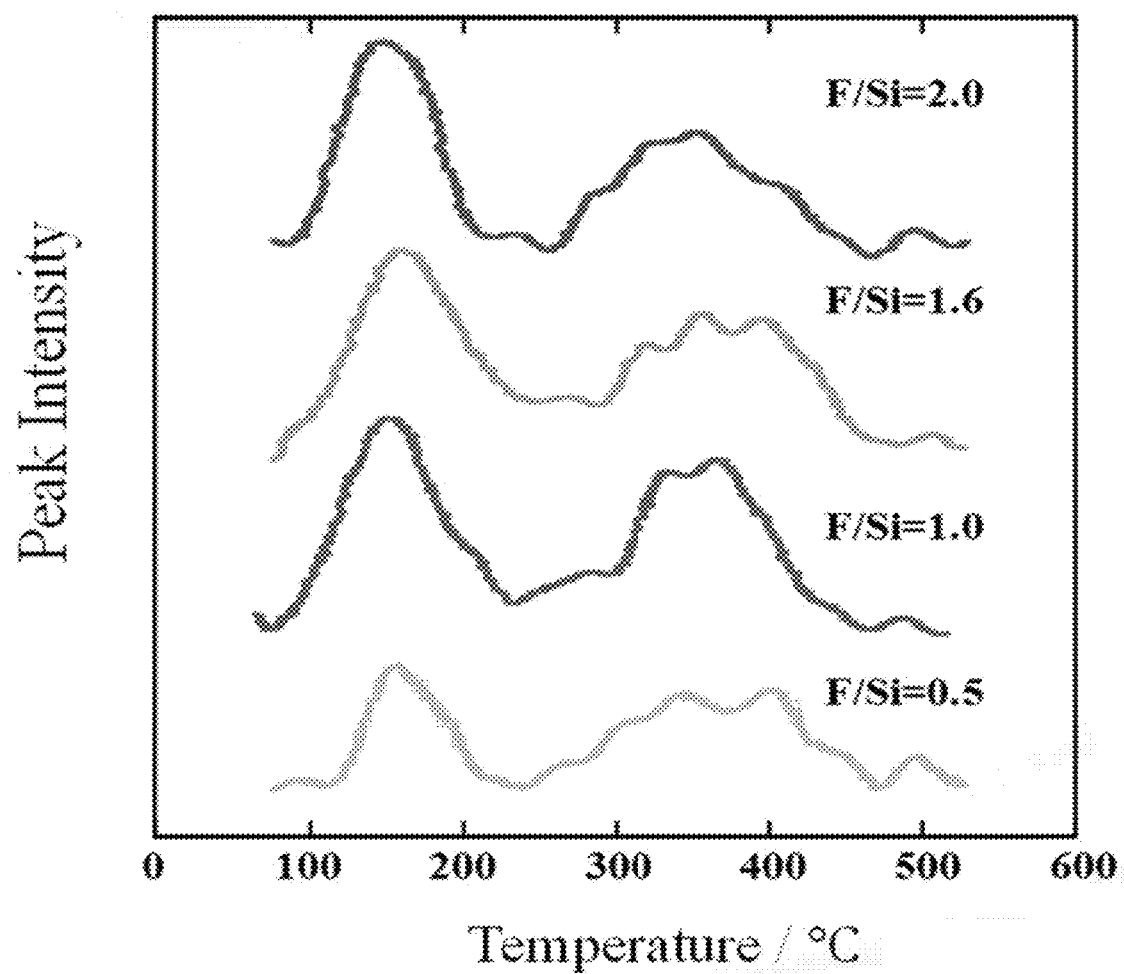
FIG. 2 shows the $NH_3$-TPD profiles of fluoride functionalized zeolite catalysts.

Embodiments of the present disclosure will now be described more fully hereinafter with reference to the accompanying drawings, in which some, but not all embodiments of the disclosure are shown.

The present disclosure will be better understood with reference to the following definitions. As used herein, the words "a" and "an" and the like carry the meaning of "one or more." Within the description of this disclosure, where a numerical limit or range is stated, the endpoints are included unless stated otherwise.

As used herein, the words "about," "approximately," or "substantially similar" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), or +/−20% of the stated value (or range of values). Within the description of this disclosure, where a numerical limit or range is stated, the endpoints are included unless stated otherwise. Also, all values and subranges within a numerical limit or range are specifically included as if explicitly written out.

As used herein, "compound" is intended to refer to a chemical entity, whether as a solid, liquid, or gas, and whether in a crude mixture or isolated and purified.

As used herein, "composite" refers to a combination of two or more distinct constituent materials into one. The individual components, on an atomic level, remain separate and distinct within the finished structure. The materials may have different physical or chemical properties, that when combined, produce a material with characteristics different from the original components. In some embodiments, a composite may have at least two constituent materials that comprise the same empirical formula but are distinguished by different densities, crystal phases, or a lack of a crystal phase (i.e. an amorphous phase).

The present disclosure is intended to include all hydration states of a given compound or formula, unless otherwise noted or when heating a material. For example, aluminum sulfate, $Al_2(SO_4)_3$, includes anhydrous $Al_2(SO_4)_3$, $Al_2(SO_4)_3 \cdot 18H_2O$, and any other hydrated forms or mixtures.

In addition, the present disclosure is intended to include all isotopes of atoms occurring in the present compounds and complexes. Isotopes include those atoms having the same atomic number but different mass numbers. By way of general example, and without limitation, isotopes of hydrogen include deuterium and tritium. Isotopes of carbon include $^{13}C$ and $^{14}C$. Isotopes of nitrogen include $^{14}N$ and $^{15}N$. Isotopes of oxygen include $^{16}O$, $^{17}O$, and $^{18}O$. Isotopes of silicon include $^{28}Si$, $^{29}Si$, and $^{30}Si$. Isotopically-labeled compounds of the disclosure may generally be prepared by conventional techniques known to those skilled in the art or by processes analogous to those described herein, using an appropriate isotopically-labeled reagent in place of the non-labeled reagent otherwise employed.

For purposes of the present invention, the Si/Al ratio refers to the Si/Al atomic ratio of the overall crystalline zeolite material and not just the MFI framework.

According to a first aspect, the present disclosure relates to a method for producing a fluoride functionalized zeolite catalyst. Zeolites are porous aluminosilicate minerals that may be found in nature or synthesized. Elementary building units of zeolites are $SiO_4$ and $AlO_4$ tetrahedra. Adjacent tetrahedra are linked at their corners via a common oxygen atom, which results in an inorganic macromolecule with a three-dimensional framework. The three-dimensional framework of a zeolite also comprises channels, channel intersections, and/or cages having dimensions in the range of 0.1-10 nm, preferably 0.2-5 nm, more preferably 0.2-2 nm. Water molecules may be present inside these channels, channel intersections, and/or cages.

In one embodiment, the fluoride functionalized zeolite catalyst of the present disclosure may have a zeolite framework of, or similar to, amicite, ammonioleucite, analcime, barrerite, brewsterite, bellbergite, bikitaite, boggsite, chabazite, chiavennite, clinoptilolite, cowlesite, dachiardite, edingtonite, epistilbite, erionite, faujasite, ferrierite, garronite, gaultite, gismondine, gmelinite, gobbinsite, gonnardite, goosecreekite, gottardiite, harmotome, heulandite, hsianghualite, kalborsite, laumontite, leucite, lévyne, lovdarite, marciopaite, mazzite, merlinoite, mesolite, montesommaite, mordenite, mutinaite, nabesite, natrolite, offretite, pahasapaite, paranatrolite, parthéite, paulingite, perlialite, phillipsite, pollucite, roggianite, scolecite, stellerite, stilbite, terranovaite, tetranatrolite, thomsonite, tschernichite, tschortnerite, tvedalite, wairakite, weinebeneite, willhendersonite, yugawaralite, and combinations thereof. In another embodiment, the fluoride functionalized zeolite catalyst may have a zeolite framework similar to a synthetic crystalline aluminosilicate, such as zeolites having the trademarked names of ZEOLITE A, ZEOLITE X, ZEOLITE Y, ZEOLITE K-G, ZEOLITE ZK5, ZEOLITE BETA, ZEOLITE ZK-4, SAPO, ALPO, USY, ZEOLITE ZSM-5 ("ZEOLITES SOCONY MOBIL-5" also called more simply, ZSM-5), ZSM-11, ZSM-12, ZSM-20, ZSM-23, ZSM-35, ZSM-38, ZSM-50, and combinations thereof. Preferably, the fluoride functionalized zeolite catalyst has a zeolite ZSM-5 framework. In a preferred embodiment, the fluoride functionalized zeolite catalyst is a ZSM-5 type zeolite. In an alternative embodiment, some other catalyst may be used that is not a zeolite, such as amorphous silica-alumina.

ZSM-5 type zeolites are composed of several pentasil units linked together by oxygen bridges to form pentasil chains. ZSM-5 type zeolites may also be considered as having an MFI framework type. A pentasil unit consists of eight five-membered rings. In these rings, the vertices are Al or Si and an O is assumed to be bonded between the vertices. The pentasil chains are interconnected by oxygen bridges to form corrugated sheets with 10-ring holes. Like the pentasil units, each 10-ring hole has Al or Si as vertices with an O assumed to be bonded between each vertex. Each corrugated sheet is connected by oxygen bridges to form a structure with straight 10-ring channels running parallel to the corrugations and sinusoidal 10-ring channels perpendicular to the sheets. Adjacent layers of the sheets are related by an inversion point. The estimated pore size of the channel running parallel with the corrugations is 5.4-5.6 Å. The crystallographic unit cell of ZSM-5 has 96 T sites (Si or Al, the zeolite being based on $TO_4$ tetrahedra geometry), 192 O sites, and a number of compensating cations depending on the Si/Al ratio, which ranges from 12 to infinity. The structure is orthorhombic (space group Pnma) at high temperatures, but a phase transition to the monoclinic space group $P2_1/n.1.13$ occurs upon cooling below a transition temperature between 300 and 350 K.

ZSM-5 type zeolites have a high ratio of silicon to aluminum. Whenever an $Al^{3+}$ cation replaces a $Si^{4+}$ cation, an additional positive charge is required to keep the material charge-neutral. With a proton ($H^+$) as the cation, the material becomes very acidic. Thus, the acidity is proportional to the Al content. The very regular 3-D structure and the acidity of ZSM-5 type zeolites may be utilized for acid-catalyzed reactions such as hydrocarbon isomerization, cracking, and alkylation. The pore sizes of ZSM-5 type zeolites may be used to impart size-selectivity into the catalytic reactions. ZSM-5 type zeolites may also be used as a support material for catalysis, for example, by being coated or decorated with one or more catalytically active metals.

ZSM-5 zeolites may be used either in the alkali metal form, e.g., the sodium form, the ammonium form, the hydrogen form, or another univalent or multivalent cationic form. Preferably, the hydrogen form (acidic form) is employed. They may also be used in intimate combination with a hydrogenating component such as tungsten, vanadium, molybdenum, rhenium, nickel, cobalt, chromium, manganese, or a noble metal such as platinum or palladium where a hydrogenation dehydrogenation function is to be performed. Such component may be exchanged into the composition, impregnated therein, or physically intimately admixed therewith. Such component may be impregnated in or on to ZSM-5 such as, for example, by, in the case of platinum, treating the zeolite with a platinum metal-containing ion. Thus, suitable platinum compounds include chloroplatinic acid, platinous chloride, and various compounds containing a platinum amine complex.

In a preferred embodiment, the fluoride functionalized zeolite catalyst is in an acidic form, which protonates light olefin compounds. This initiates acid-catalyzed reactions, especially hydrocarbon cracking. The acidity or number of acid sites of the fluoride functionalized zeolite catalyst may be measured by a liquid phase ion exchange method, a gas-phase temperature programmed desorption method, or some other method. In one embodiment, a liquid phase ion exchange/filtrate titration method is used to determine an acidity of the fluoride functionalized zeolite catalyst. In this method the fluoride functionalized zeolite catalyst is first calcined in air and then subjected to an ion exchange treatment in the presence of an aqueous sodium chloride solution. After the treatment, the solution is filtered to obtain a filtrate. The filtrate is washed with pure/deionized water, and the whole amount of the washing liquid is collected and further mixed with the aforementioned filtrate. The acidity of the resulting mixed solution (i.e. filtrate+washing liquid) is measured by neutralization titration, and a moles acid per gram of the fluoride functionalized zeolite catalyst is reported as the acidity of the zeolite. Alternatively, in a preferred embodiment, an ammonia temperature-programmed desorption ($NH_3$-TPD) method is used to measure an acidity of the fluoride functionalized zeolite catalyst. Here, a predetermined amount of the fluoride functionalized zeolite catalyst may be pretreated at 500° C. in the presence of helium for at least 60 minutes, preferably 90 minutes. Then, the fluoride functionalized zeolite catalyst may be treated at 100° C. in an atmosphere containing helium and 5-15 vol %, preferably 5-10 vol % of ammonia. After that, the fluoride functionalized zeolite catalyst is heated at a temperature ramping rate of 10° C./min from 100° C. to 600° C., wherein ammonia is desorbed, and the amount of desorbed ammonia (measured by a thermogravimetric analyzer) is used to determine the acidity of the fluoride functionalized zeolite catalyst.

In one embodiment, the fluoride functionalized zeolite catalyst has a total acidity of 0.017-0.020 mmol/g, preferably 0.017-0.020 mmol/g, more preferably 0.017-0.020 mmol/g as defined by $NH_3$-TPD, though in some embodiments, the fluoride functionalized zeolite catalyst may have a total acidity of less than 0.017 mmol/g or greater than 0.020 mmol/g. Preferably the total acidity, or the number of acid sites per gram catalyst, is considered equivalent to the number of ammonia molecules per gram catalyst that desorb.

In one embodiment, the ammonia may desorb in two populations as the fluoride functionalized zeolite catalyst is heated, due to the different strengths, availabilities, or geometries of the acid binding sites within the zeolite structure. One population may desorb at a temperature of 80-260° C., preferably 90-240° C., and another population may desorb at a temperature of 260-550° C., preferably 270-480° C. At the lower temperature range, weakly bounded ammonia may be desorbed at an amount of 0.0040-0.0120 mmol/g, preferably 0.0060-0.0110 mmol/g, more preferably 0.0080-0.0100 mmol/g, though in some embodiments, less than 0.0040 mmol/g or greater than 0.0120 mmol/g may desorb from the zeolite. At the higher temperature range, 0.0080-0.0120 mmol/g, preferably 0.0082-0.0115 mmol/g, more preferably 0.0085-0.0197 mmol/g may desorb, though desorption of less than 0.0080 mmol/g or greater than 0.0120 mmol/g may be possible in other embodiments.

In one embodiment, the fluoride functionalized zeolite catalyst has a surface area of 330-400 m$^2$/g, preferably 350-380 m$^2$/g, more preferably 355-365 m$^2$/g, though in some embodiments, the fluoride functionalized zeolite catalyst may have a surface area of less than 330-400 m$^2$/g or greater than 400 m$^2$/g. In a preferred embodiment, the fluoride functionalized zeolite catalyst is porous, with a total pore volume of 0.15-0.21 cm$^3$/g, preferably 0.16-0.20 cm$^3$/g, more preferably 0.17-0.19 cm$^3$/g. However, in some embodiments, the fluoride functionalized zeolite catalyst may have a total pore volume of less than 0.15 cm$^3$/g or greater than 0.21 cm$^3$/g.

In one embodiment, the high surface area and porosity of the fluoride functionalized zeolite catalyst may be contributed by both micro-pores and meso-pores. In one embodiment, the fluoride functionalized zeolite catalyst may have micro-pores (i.e. pores with an average pore diameter of less than 2 nm) having a specific pore volume in the range of 0.1-0.3 cm$^3$/g, preferably 0.1-0.2 cm$^3$/g, more preferably 0.15-0.2 cm$^3$/g. Preferably, an average pore diameter of the fluoride functionalized zeolite catalyst is within the range of 4-12 Å, preferably 5-8 Å, more preferably 5-6.5 Å. The fluoride functionalized zeolite catalyst may further include meso-pores (i.e. pores with an average pore diameters in the range of 2-50 nm, preferably 2-20 nm) having a specific pore volume in the range of 0.01-0.15 cm$^3$/g, preferably 0.05-0.15 cm$^3$/g, more preferably 0.05-0.1 cm$^3$/g. In one embodiment, a specific surface area of the micro-pores in the fluoride functionalized zeolite catalyst is in the range of 100-500 m$^2$/g, preferably 300-500 m$^2$/g, more preferably about 400 m$^2$/g, whereas a specific surface area of the meso-pores in the fluoride functionalized zeolite catalyst is in the range of 50-150 m$^2$/g, preferably 50-100 m$^2$/g, more preferably about 80 m$^2$/g. The fluoride functionalized zeolite catalyst may be in the form of pellets having a diameter in the range of 0.5-5 mm, preferably 0.5-1.5 mm, more preferably about 1 mm. The fluoride functionalized zeolite catalyst may be extrudated to have a geometry selected from the group consisting of cylindrical, rectilinear, star-shaped, conical, pyramidal, rectangular, cubical, and ring-shaped.

As mentioned earlier, a first aspect of the present disclosure relates to a method for producing a fluoride functionalized zeolite catalyst. The method involves the step of mixing a structure directing agent, an inorganic fluoride salt, an aluminum salt, a silicating agent, and water to form a gel. The gel is heated to produce a crystallized product, and then calcined in air to produce the fluoride functionalized zeolite catalyst.

In a preferred embodiment, the structure directing agent, the inorganic fluoride salt, the aluminum salt, and water are mixed to form an aqueous solution, and then the silicating agent is mixed with the aqueous solution to form the gel. In other embodiments, the components of the gel may be mixed in different orders. Preferably, the components are mixed to form a homogeneous gel. As defined here, a gel is a non-fluid colloidal network or polymer network that is expanded throughout its whole volume by a fluid. A gel may be thought of as a solid jelly-like material comprised of a substantially dilute cross-linked system, which exhibits no flow when in the steady-state. By weight, gels are mostly liquid, and in this way gels are a dispersion of molecules of a liquid within a solid. In an alternative embodiment, the fluoride functionalized zeolite catalyst may be made from a mixture without the mixture forming a gel.

In one embodiment, the gel may comprise the structure directing agent at a weight percentage of 1-10 wt %, preferably 2-7 wt %, more preferably 3.5-5.5 wt %, relative to a total weight of the gel. However, in some embodiments, the gel may comprise the structure directing agent at a weight percentage lower than 1 wt % or greater than 10 wt %.

In one embodiment, the gel may comprise the inorganic fluoride salt at a weight percentage of 0.1-2.0 wt %, preferably 0.4-1.5 wt %, more preferably 0.6-1.0 wt %, relative to a total weight of the gel. However, in some embodiments, the gel may comprise the inorganic fluoride salt at a weight percentage of less than 0.1 wt % or greater than 2.0 wt %.

In one embodiment, the gel may comprise the aluminum salt at a weight percentage of 0.01-1.00 wt %, preferably 0.05-0.50 wt %, more preferably 0.06-0.10 wt %, relative to a total weight of the gel. However, in some embodiments, the gel may comprise the aluminum salt at a weight percentage of less than 0.01 wt %, or greater than 1.00 wt %.

In one embodiment, the gel may comprise the silicating agent at a weight percentage of 10-17 wt %, preferably 11-15 wt %, more preferably 12-14 wt %, relative to a total weight of the gel. However, in some embodiments, the gel may comprise the silicating agent at a weight percentage of less than 10 wt % or greater than 17 wt %.

In one embodiment, the gel may comprise water at a weight percentage of 70-90 wt %, preferably 72-88 wt %, more preferably 75-85 wt %, relative to a total weight of the gel. However, in some embodiments, the gel may comprise water at a weight percentage of less than 70 wt % or greater than 90 wt %.

In one embodiment, the gel has a F to Si molar ratio of 0.1:1.0-3.0:1.0, preferably 0.5:1.0-2.5:1.0, more preferably 1.5:1.0-2.1:1.0, or about 2.0:1.0. In other embodiments, the gel may have a F to Si molar ratio of less than 0.1:1.0 or greater than 3.0:1.0. In one embodiment, the fluoride functionalized zeolite catalyst may have a F to Si molar ratio of those ranges just discussed for the gel.

In one embodiment, a relative molar composition of the gel may be 1 Si: (0.05-0.12) structure directing agent: (0.0001-0.0030) Al: (0.1-3.0) F: (10-40) H$_2$O. In another embodiment, a relative molar composition of the gel may be about 1 SiO$_2$: (0.06-0.10) TPABr: (0.0001-0.0015) Al$_2$O$_3$: (0.2-2.5) NH$_4$F: (15-35) H$_2$O. In a preferred embodiment, a relative molar composition of the gel may be about 1 SiO$_2$: 0.08 TPABr: 0.0005 Al$_2$O$_3$: (0.5-2.0) NH$_4$F: 20 H$_2$O.

In one embodiment, the structure directing agent is a quaternary ammonium salt with a chemical formula N(C$_n$H$_{3n}$)$_4$$^+$X$^-$. X is a halide ion or a hydroxide, and n is an integer from 1 to 5. Exemplary halide ions include but are not limited to, fluoride, chloride, bromide, and iodide. Accordingly, exemplary structure directing agents include but are not limited to tetramethylammonium hydroxide, tetraethylammonium hydroxide, tetrapropylammonium hydroxide, tetrabutylammonium hydroxide, tetrapentylammonium hydroxide, tetramethylammonium fluoride, tetraethylammonium fluoride, tetrapropylammonium fluoride, tetrabutylammonium fluoride, tetrapentylammonium fluoride, tetramethylammonium chloride, tetraethylammonium chloride, tetrapropylammonium chloride, tetrabutylammonium chloride, tetrapentylammonium chloride, tetramethylammonium bromide, tetraethylammonium bromide, tetrapropylammonium bromide, tetrabutylammonium bromide, tetrapentylammonium bromide, tetramethylammonium iodide, tetraethylammonium iodide, tetrapropylammonium iodide, tetrabutylammonium iodide, tetrapentylammonium iodide. In a preferred embodiment, the halide ion is bromide, and the structure directing agent is tetrapropylammonium bromide (TPABr). In an alternative embodiment, the structure directing agent is cetyltrimethylammonium chloride, cetyltrimethylammonium bromide, cetyltrimethylammonium iodide, cetyltriethylammonium bromide, cetyltriethylammonium chloride, cetyltriethylammonium iodide, or any combination thereof.

The term "inorganic fluoride salt" refers to a chemical compound consisting of an inorganic cation and a fluoride anion. Preferably the inorganic fluoride salt is ammonium fluoride ($NH_4F$) and/or ammonium bifluoride ($NH_4HF_2$). In one embodiment, the inorganic fluoride salt is ammonium fluoride ($NH_4F$). In an alternative embodiment, the inorganic fluoride salt may be NaF, $CaF_2$, KF, HF, $MgF_2$, LiF, $Na_3AlF_6$, $AlF_3$, $Na_2SiF_6$, boron trifluoride, ammonium fluoborate, ammonium fluosilicate, or some other salt. In another alternative embodiment, an organic fluoride salt may be used instead of an inorganic fluoride salt. The organic fluoride salt may be tetramethylammonium fluoride, tetraethylammonium fluoride, tetrapropylammonium fluoride, tetrabutylammonium fluoride, or some other organic fluoride salt. In another embodiment, a single compound comprising fluoride, such as tetrapropylammonium fluoride, may be used both in place of the inorganic fluoride salt and as the structure directing agent.

In an alternative embodiment, sodium hydroxide may be utilized as a replacement for the fluoride salt. Alternatively, sodium hydroxide may also be used in combination with ammonium fluoride ($NH_4F$) and/or ammonium bifluoride ($NH_4HF_2$).

In one embodiment, the gel and the fluoride functionalized zeolite catalyst are substantially free of phosphorous and sodium. As defined here, the gel and the fluoride functionalized zeolite catalyst being substantially free of phosphorous and sodium means that the gel and the fluoride functionalized zeolite catalyst each comprises less than 0.1 wt %, preferably less than 0.01 wt %, more preferably less than 0.005 wt % sodium and phosphorous per relative to a total weight of the gel or the fluoride functionalized zeolite catalyst. In an alternative embodiment, the gel or the fluoride functionalized zeolite catalyst may comprise sodium and/or phosphorous at 0.2-1 wt %, 1-5 wt %, or 5-10 wt % relative to a total weight of the gel or the fluoride functionalized zeolite catalyst. In this alternative embodiment, a compound comprising sodium and/or a compound comprising potassium may be added during the mixing of the gel, or after the mixing of the gel; during the synthesis of the fluoride functionalized zeolite catalyst or after the synthesis of the fluoride functionalized zeolite catalyst.

In one embodiment, the aluminum salt is aluminum nitrate or aluminum sulfate. The aluminum salt may be hydrated or anhydrous. Preferably the aluminum salt is hydrated. In other embodiments, the aluminum salt may be aluminum oxide, aluminum isopropoxide, aluminum borohydride, aluminum acetate, or some other aluminum salt.

In one embodiment, the fluoride functionalized zeolite catalyst has a Si to Al molar ratio of 500:1-2,000:1, preferably 750:1-1,500:1, more preferably 900:1-1,300:1, or 1,000:1-1,200:1. However, in some embodiments, the fluoride functionalized zeolite catalyst may have a Si to Al molar ratio of less than 500:1 or greater than 2,000:1.

In one embodiment, the fluoride functionalized zeolite catalyst has an average crystal size of 0.1-50 µm, preferably 1-40 µm, more preferably 5-30 µm, though in some embodiments, the fluoride functionalized zeolite catalyst may have an average crystal size of smaller than 0.1 µm or greater than 50 µm. In one embodiment, a plurality of crystals may be agglomerated or aggregated into larger particles, for instance, particles having an average particle diameter of 0.1-5.0 mm, preferably 0.2-2.5 mm, more preferably 0.4-1.2 mm. In other embodiments, the crystals of the zeolite catalyst may be agglomerated or aggregated into particles having an average particle diameter of less than 0.1 mm or greater than 5.0 mm.

In one embodiment, the silicating agent is at least one selected from the group consisting of tetraethylorthosilicate (TEOS), tetramethylorthosilicate (TMOS), silica ($SiO_2$), and polydimethylsiloxane (PDMS). Preferably, the silicating agent is silica, and may be in the form of fused quartz, fumed silica, silica gel, precipitated silica, amorphous silica, mesoporous silica, or aerogel. Preferably the silica is in the form of fumed silica. Fumed silica, also known as pyrogenic silica, comprises microscopic droplets of amorphous silica fused into branched, chainlike, three-dimensional secondary particles which then agglomerate into tertiary particles. Fumed silica generally has a low bulk density of about 160-190 kg/m$^3$, and a high surface area of about 50-600 m$^2$/g. In alternative embodiments, silicate, sodium silicate, tetramethylammonium silicate, and/or sodium metasilicate may be utilized in conjunction as the silicating agent or in conjunction with a silicating agent previously mentioned.

The water may be tap water, distilled water, bidistilled water, deionized water, deionized distilled water, reverse osmosis water, and/or some other water. In one embodiment the water is bidistilled to eliminate trace metals. Preferably the water is bidistilled, deionized, deionized distilled, or reverse osmosis water and at 25° C. has a conductivity at less than 10 µS·cm$^{-1}$, preferably less than 1 µS·cm$^{-1}$; a resistivity greater than 0.1 MΩ·cm, preferably greater than 1 MΩ·cm, more preferably greater than 10 MΩ·cm; a total solid concentration less than 5 mg/kg, preferably less than 1 mg/kg; and a total organic carbon concentration less than 1000 µg/L, preferably less than 200 µg/L, more preferably less than 50 µg/L.

After mixing to form the gel, the gel may be heated at 180-250° C., preferably 190-230° C., more preferably 195-210° C. for 12-72 h, preferably 24-56 h, more preferably 36-50 h to produce a crystallized product. Preferably the gel may be heated at pressures higher than 1 atm, for instance, 5-35 atm, or 10-20 atm, and may be heated in an autoclave. However, in other embodiments, the gel may be heated at a temperature lower than 180° C. or greater than 250° C. and/or for a time shorter than 12 h or longer than 72 h. In a preferred embodiment, the gel may be heated at about 200° C. for about 2 days. This heating step may be considered as subjecting the gel to a hydrothermal crystallization process.

The crystallized product may be washed with water and/or an organic solvent such as acetone, methanol, ethanol, or isopropanol. A crystallized product that was washed may then be dried in an oven at 50-120° C., preferably 60-100° C., more preferably 70-90° C. for 6-24 h, preferably 12-18 h, though in some embodiments, the crystallized product may be dried at a temperature of lower than 50° C. or greater than 120° C., and/or shorter than 6 h or longer than 24 h.

The crystallized product may be calcined by heating in air at 600-850° C., preferably 675-825° C., more preferably 725-775° C. for 3-12 h, preferably 4-10 h, more preferably 5-7 h to produce the fluoride functionalized zeolite catalyst. In other embodiments, the crystallized product may be calcined by heating in air at a temperature of lower than 600° C. or higher than 850° C., and/or for a time shorter than 3 h or longer than 12 h. In one embodiment, the crystallized product may be calcined in an environment other than air, for instance, oxygen-enriched air. In another embodiment, a crystallized product that was washed may be dried and consecutively calcined in the same oven or heating device. Preferably the crystallized product is not placed immediately in an oven or furnace at the calcination temperature, but instead heated gradually to the calcination temperature, for instance, at a heating rate of 1-7° C./min, preferably 3-5° C./min. Preferably, following the calcination, the fluoride functionalized zeolite catalyst is allowed to gradually cool in order to avoid sudden temperature changes. According to a second aspect, the present disclosure relates to a fluoride functionalized zeolite catalyst produced by the method discussed above.

According to a third aspect, the present disclosure relates to a method of using a fluoride functionalized zeolite catalyst to convert a $C_4$-$C_6$ olefin into ethylene, propylene, and/or butylene. The method involves contacting a gas stream of the $C_4$-$C_6$ olefin with the fluoride functionalized zeolite catalyst at a temperature of 400-700° C. to produce ethylene, propylene, and/or butylene. Here, the fluoride functionalized zeolite catalyst has a F to Si molar ratio of 0.1:1.0-3.0:1.0 and an average particle size of 0.1-5.0 mm. Additionally, at least 75 mol % of the $C_4$-$C_6$ olefin present is converted to ethylene, propylene, and/or butylene.

In one embodiment, the gas stream of the $C_4$-$C_6$ olefin may be a low value refinery or petrochemical hydrocarbon feed stream, such as steam cracker by-products rich in $C_4$'s and pygas, which otherwise have poor propylene selectivity when recycled to a steam cracker. In one embodiment, the gas stream of the $C_4$-$C_6$ olefin comprises 30-95 wt %, preferably 40-85 wt % of one or more alkenes having 4 to 6 carbon atoms. The term "olefin" as used herein refers to unsaturated straight-chain hydrocarbons, unsaturated branched hydrocarbons, or cyclic unsaturated hydrocarbons. In one embodiment, the $C_4$-$C_6$ olefin is selected from the group consisting of isomers of butene, isomers of pentene, and/or isomers of hexene. In one embodiment, the $C_4$-$C_6$ olefin is selected from the group consisting of 1-butene, cis- and trans-2-butene, butadiene, pentene, pentadiene, hexene, and benzene. In another embodiment, the $C_4$-$C_6$ olefin is 1-butene, 1-pentene, and/or 1-hexene. In a preferred embodiment, the $C_4$-$C_6$ olefin is 1-hexene.

In another embodiment, the gas stream may comprise hydrocarbons that are not $C_4$-$C_6$ olefins. For instance, in one alternative embodiment, the gas stream may comprise olefins having 7 or more carbon atoms. In another alternative embodiment, the gas stream may comprise one or more aliphatic hydrocarbons having 3-10, or 4-8 carbon atoms. The hydrocarbons may be straight chain, open chain, or cyclic, and may be saturated or unsaturated. Such hydrocarbons may include n-butane, n-butenes, isobutane, isobutene, straight chain, branched chain and cyclic, pentanes, pentenes, hexanes, hexenes, heptanes, heptenes, toluene, propane, propylene, xylene, and ethylbenzene. In other embodiments, the gas stream of the present invention may include light naphthas or raffinates, containing sufficient amounts of $C_4$-$C_7$ olefins and/or paraffins, $C_4$-$C_7$ cuts from light naphthas or raffinates, catalytically cracked naphtha, coker naphtha, steam, steam cracker pyrolysis gasoline, synthetic chemical streams containing sufficient amounts of $C_4$-$C_7$ olefins and/or paraffins or any other hydrocarbons containing sufficient amounts of $C_4$-$C_7$ olefins and/or paraffins. Gas streams comprising high levels of dienes, sulfur, nitrogen, and oxygenates are preferably selectively hydrotreated prior to contacting with the fluoride functionalized zeolite catalyst. However, certain gas streams with low levels of dienes, sulfur, nitrogen, metal compounds, and oxygenates may be processed directly from FCC units, cokers, or steam crackers without any pretreatment.

As mentioned earlier, at least 75 mol % of the $C_4$-$C_6$ olefin present is converted to ethylene, propylene, and/or butylene, relative to the total moles of $C_4$-$C_6$ olefin initially present. In other words, the conversion of the $C_4$-$C_6$ olefin is at least 75%. In another embodiment, the conversion of the $C_4$-$C_6$ olefin is at least 80%, preferably at least 85%, more preferably at least 90%, even more preferably at least 95%, though in some embodiments, the conversion may be lower than 75%. In one preferred embodiment, at least 85 mol % of the $C_4$-$C_6$ olefin present is converted to ethylene, propylene, and/or butylene.

In one embodiment, the $C_4$-$C_6$ olefin may be converted to a mixture of ethylene, propylene, and/or butylene. For instance, relative to the total weight of the $C_4$-$C_6$ olefin converted, 1-15 wt %, preferably 2-10 wt % may be converted to ethylene; 5-25 wt %, preferably 10-20 wt % may be converted to butylene, and 60-85 wt %, preferably 62-75 wt % may be converted to propylene. Other products such as hydrogen gas, pentene, and methane may also be produced.

In one embodiment, the $C_4$-$C_6$ olefin is 1-hexene, and a mole percentage of propylene produced with respect to moles 1-hexene consumed is 60-85%, preferably 62-82%, more preferably 65-80%. This mole percentage may be considered as the selectivity of propylene. In other embodiments, however, the $C_4$-$C_6$ olefin may be 1-hexene while the selectivity of propylene is lower than 60% or greater than 85%. In one embodiment, the selectivity of propylene may be increased over different fluoride functionalized zeolite catalysts as the F/Si ratio is increased. In an alternative embodiment, the selectivity of propylene may be tuned by changing the pore size of a zeolite catalyst, or by functionalizing a fluoride functionalized zeolite catalyst or some other zeolite catalyst with different chemical groups.

A yield of a product may be determined by multiplying the conversion percentage of the reactant (here, the $C_4$-$C_6$ olefin), with the selectivity of the product. In one embodiment, a product is propylene, and is produced with a yield of 60-95%, preferably 62-90%, more preferably 65-80%. However, in some embodiments, propylene may be produced with a yield of lower than 60% or greater than 95%.

In one embodiment, the $C_4$-$C_6$ olefin is present in the gas stream at a partial pressure of 20-500 kPa, preferably 30-400 kPa, more preferably 35-345 kPa, even more preferably 50-300 kPa. However, in some embodiments, the $C_4$-$C_6$ olefin may be present in the gas stream at a partial pressure of less than 20 kPa or greater than 500 kPa. In one embodiment, the total pressure of the gas stream may be 50-600 kPa, preferably 100-500 kPa, more preferably 100-400 kPa, even more preferably 100-300 kPa, though in other embodiments, the total pressure of the gas stream may be lower than 50 kPa or greater than 600 kPa. In one embodiment, the total pressure of the gas stream may be about atmospheric pressure, or about 101 kPa. In one embodiment, the $C_4$-$C_6$ olefin may be present at a partial pressure that changes throughout the course of the catalytic reaction.

In one embodiment, the gas stream comprises an inert carrier gas. The inert carrier gas may be helium, nitrogen, argon, or some other inert gas. Preferably the inert carrier gas is nitrogen. In other embodiments, the gas stream may comprise a carrier gas that is not considered an inert gas, such as air, steam, or carbon dioxide.

In one embodiment, the fluoride functionalized zeolite catalyst is substantially free of phosphorous and sodium. As defined here, the fluoride functionalized zeolite catalyst being substantially free of phosphorous and sodium means that the fluoride functionalized zeolite catalyst comprises less than 0.1 wt %, preferably less than 0.01 wt %, more preferably less than 0.005 wt % sodium and phosphorous relative to a total weight of the fluoride functionalized zeolite catalyst. In an alternative embodiment, the fluoride functionalized zeolite catalyst may comprise sodium and/or phosphorous at 0.2-1 wt %, 1-5 wt %, or 5-10 wt % relative to a total weight of the fluoride functionalized zeolite catalyst. In this alternative embodiment, a compound comprising sodium and/or a compound comprising potassium may be added during the synthesis of the fluoride functionalized zeolite catalyst or after the synthesis.

In one embodiment, the $C_4$-$C_6$ olefin is fed to a fixed bed reactor at a flow rate of 5-20 mL/h per g fluoride functionalized zeolite catalyst, preferably 7-18 mL/h per g fluoride functionalized zeolite catalyst, more preferably 9-13 mL/h per g fluoride functionalized zeolite catalyst. In a preferred embodiment, the $C_4$-$C_6$ olefin is fed to a fixed bed reactor at a flow rate of about 12 mL/h per g fluoride functionalized zeolite catalyst, though in other embodiments, the $C_4$-$C_6$ olefin may be fed to the fixed bed reactor at a flow rate of less than 5 mL/h per g, or greater than 20 mL/h per g fluoride functionalized zeolite catalyst.

In one embodiment, the $C_4$-$C_6$ olefin may be fed to a reactor with a gas hourly space velocity (GHSV) of 400-15,000 $hr^{-1}$, preferably 800-10,000 $hr^{-1}$, more preferably 1,000-5,000 $hr^{-1}$, even more preferably 1,200-3,000 $hr^{-1}$. However, in some embodiments, the $C_4$-$C_6$ olefin may be fed to a reactor with a GHSV of less than 400 $hr^{-1}$ or greater than 15,000 $hr^{-1}$.

In one embodiment, the $C_4$-$C_6$ olefin may be fed to the fluoride functionalized zeolite catalyst at a W/F ratio (catalyst weight/feed flow rate) of 0.05-0.30 h, preferably 0.08-0.25 h, more preferably 0.10-0.20 h, or about 0.125 h. However, in other embodiments, the olefin may be fed to the fluoride functionalized zeolite catalyst at a W/F ratio of less than 0.05 h or greater than 0.30 h.

According to a second aspect of the disclosure, the present disclosure relates to a fluoride functionalized zeolite catalyst created by the method of the first aspect of the disclosure.

In one embodiment, the method of the third aspect of the disclosure uses a fluoride functionalized zeolite catalyst created by or substantially similar to the fluoride functionalized zeolite catalyst of the first aspect of the disclosure.

"Contacting," as used herein refers to a process whereby a vaporized-state of the $C_4$-$C_6$ olefin in the gas stream is directly contacted with the fluoride functionalized zeolite catalyst present in a catalyst bed of a reactor at reaction conditions that are favored for catalytic reactions to take place. The $C_4$-$C_6$ olefin may be contacted with the catalyst by passing through the catalyst or by passing over the catalyst (e.g. a vaporized-state of the $C_4$-$C_6$ olefin as an atmosphere to the catalyst). Additionally, the $C_4$-$C_6$ olefin may be contacted with the catalyst by mixing the $C_4$-$C_6$ olefin and the fluoride functionalized zeolite catalyst as a heterogeneous solution. Among these, the preferred contacting is by passing the gas stream of the $C_4$-$C_6$ olefin through the fluoride functionalized zeolite catalyst, for example as a catalyst bed. In other embodiments, the contacting may be accomplished by any conventional technique, for example, by using the fluoride functionalized zeolite catalyst in a fixed bed system, a moving bed system, a fluidized bed system, or in a batch type operation. In one embodiment, the fluoride functionalized zeolite catalyst, as part of a catalyst bed or separate, may be attached or embedded in a support or matrix material such as silica, alumina, silica-alumina, clay, and mixtures thereof.

The "catalyst bed" as used herein refers to a container with an internal cavity that is filled with the fluoride functionalized zeolite catalyst. Examples of the catalyst beds include, but are not limited to a hollow tube, a pipe, a duct, etc. The reactor may preferably be a cylindrical vessel with the catalyst bed located inside, wherein olefin stream is contacted with the zeolite catalyst. The reactor may include one or more catalyst beds that are located in series. In a preferred embodiment, the reactor has only one catalyst bed. The reactor may have various geometries including spherical, conical, pyramidal, rectangular, or cubical geometries. In one embodiment, the reactor has a volume of less than 1 mL, preferably less than 500 µL. In another embodiment, the reactor has a volume in the range of 1-1,000 mL, preferably 10-1,000 mL, more preferably 10-100 mL. In another embodiment, the reactor has a volume in the range of 1-10,000 L, preferably 100-1,000 L, more preferably 500-1,000 L. In a preferred embodiment, reaction conditions are selected such that $C_4$-$C_6$ olefins present in the gas stream are converted to propylene. In alternative embodiments, the catalytic reactions may also include transalkylation, and/or disproportionation of the $C_4$-$C_6$ olefins. Transalkylation, refers to a chemical reaction through which one or more alkyl groups (e.g. methyl, ethyl, propyl, butyl, etc.) are transferred from one organic compound to another. Disproportionation refers to a redox reaction in which an organic molecule is reduced in a reduction reaction, and the similar organic molecule is also oxidized in an oxidation reaction, thereby forming two different products.

In one embodiment, both the conversion percentage of a $C_4$-$C_6$ olefin, and/or some other hydrocarbon reactant in the gas stream, and the selectivity of one or more products, are sustained for a reaction period of 10-24 hours, or 12-72 hours, or at least 24 hours, preferably at least 36 hours, more preferably at least 50 hours. As defined here, a conversion percentage and a selectivity being sustained for a certain reaction period means that for a reaction period, the conversion percentage and the selectivity each vary by less than 10%, preferably less than 7%, more preferably less than 5% of each respective mean value over that period.

In one embodiment, the $C_4$-$C_6$ olefin is 1-hexene, and over a reaction period of 24-72 hours, preferably 36-60 hours, at least 85 mol %, preferably at least 90 mol %, more preferably at least 95 mol % of the 1-hexene present is converted to ethylene, propylene, and/or butylene, and a mole percentage of propylene produced with respect to moles 1-hexene converted is 60-85 mol %, preferably 62-80 mol %. In a related embodiment, the fluoride functionalized zeolite catalyst is able to sustain both the conversion of 1-hexene and the selectivity of propylene for at least 24 hours, preferably at least 36 hours, more preferably at least 50 hours. In other embodiments, the fluoride functionalized zeolite catalyst is able to sustain both the conversion of 1-hexene and the selectivity of propylene for at least 60 hours, preferably at least 72 hours, more preferably at least 84 hours.

Preferably, the fluoride functionalized zeolite catalyst has high selectivity, and under the conditions of hydrocarbon conversion provides a high percentage of desired products compared to similar zeolite catalysts that are not fluoride functionalized. In addition, the ability for the fluoride functionalized zeolite catalyst to be physically stable under high temperatures and/or high pressures is important for a cracking catalyst. During catalytic conversion, however, the cracking reaction may be accompanied by a number of other side reactions such as aromatization, polymerization, alkylation, isomerization, and the like.

As a result of these side reactions, carbonaceous deposits, referred as "coke," may be formed on the fluoride functionalized zeolite catalyst. This deposit of coke may impair the catalyst efficiency, decreasing the rate of conversion and/or decreasing the selectivity of the products. For instance, in one embodiment, the formation of coke may decrease the conversion percentage of 1-hexene and/or the selectivity of propylene. It may be possible to remove the fluoride functionalized zeolite catalyst after coke has been deposited thereon and to regenerate it by burning the coke in a stream of oxidizing gas. Alternatively, the fluoride functionalized zeolite catalyst may be regenerated in place, without being removed from a reactor. In one embodiment, the fluoride functionalized zeolite catalyst may be regenerated to remove coke by heating in a oxidizing gas stream (for instance, comprising $O_2$ gas) and at a temperature of 500° C.-900° C., preferably 600° C.-850° C. The regenerated fluoride functionalized zeolite catalyst may then be reused.

In one embodiment, a weight percentage of coke formed relative to a combined mass of a fluoride functionalized zeolite catalyst with coke is lower or divided by a factor of at least 2, preferably at least 2.5, more preferably at least 3.0, even more preferably at least 3.5 compared to a similar zeolite catalyst, without fluoride functionalization, being used under the same reaction conditions.

For instance, in one embodiment, the weight percentage of coke formed on a fluoride functionalized zeolite catalyst having a F/Si molar ratio of 1.6-2.5, preferably 1.8-2.2, may be 0.20-1.50 wt %, preferably 0.35-1.20 wt %, more preferably 0.55-0.95 wt %, relative to a combined mass of the coke and fluoride functionalized zeolite catalyst, for a reaction period of 40-60 h, preferably 45-55 h. The weight percentage of coke formed on a substantially similar, yet non-fluoride functionalized zeolite catalyst, under the same reaction conditions, may be 1.50-6.00 wt %, preferably 1.75-4.00 wt %, more preferably 2.00-3.50 wt % relative to a total weight of the zeolite catalyst and coke.

The examples below are intended to further illustrate protocols for preparing, characterizing the fluoride functionalized zeolite catalyst and uses thereof, and are not intended to limit the scope of the claims.

Example 1

ZSM-5 Synthesis with Different F/Si Ratio by Hydrothermal Method

The present invention disclosure provides a method for synthesizing active ZSM-5 catalysts (i.e. fluoride functionalized zeolite catalysts) for cracking of $C_4$-$C_6$ olefins to light olefins. The MFI crystal structure with intersecting 10 membered-ring pore channels having a $SiO_2/Al_2O_3$ ratio of 2000 were synthesized using different F/Si ratio from 0 to 2.0. Physico-chemical characterization of ZSM-5 with F/Si ratio of 0, 0.5, 1.0, 1.6, and 2.0 are presented in Table 1. All the catalyst showing similar very weak acidic sites as expected. However, catalyst B, C and D shows slightly higher than catalyst A and E. Even though the acidity of catalyst B, C and D is close, the activity of catalyst D was higher as compared to other catalysts. The conversion of 1-hexene was above 93% at 450° C. and it further increases with increase in temperature (99% at 600° C.). The yield of light olefins at 550 and 600° C. remains the same. At low temperature (450° C.), about 25% butenes formation was observed. In all the cases, a F/Si ratio of 2 showed higher activity than the other catalysts, even though the acidity of F/Si=1.0, 1.6, and 2 remains the same. Upon increasing the reaction temperature from 450 to 500° C., the formation of butenes was reduced to 17% at 550° C., and it was further decreased to 12% at 600° C. At the same time, the yield of ethylene increased as the reaction temperature increased. The higher activity catalyst D is related to the amount of fluoride ions in the synthesis of ZSM-5. The fluorine atom present in the zeolite framework creates a more hydrophilic environment in the catalyst. The hydrophilic nature and weak acid sites are found to be responsible for higher propylene selectivity.

The operating conditions of the 1-hexene cracking reaction comprise temperatures between about 350° C. to about 700° C. A preferred temperature for operating the process is within the range from about 400° C. to about 650° C. with a more preferred operating temperature of about 450° C. to about 600° C. The reaction process operation conditions further include hydrocarbon partial pressures between about 35 kPa (5 psia) to about 345 kPa (50 psia). The catalytic process of 1-hexene cracking may be conducted in a continuous circulating fluidized-bed reactor, a dense fluidized-bed reactor, a fixed-bed reactor, or in a fixed-bed swing reactor. The W/F ratio, feed rate of 1-hexene, and catalyst weight were 0.125 h, 1.8 mL/h, and 0.15 g, respectively.

The present invention is further explained in the following examples, however, this invention is not restricted to these examples.

In a typical synthesis, 4.26 g tetrapropylammonium bromide (TPABr) and 0.74 g ammonium fluoride ($NH_4F$) and 0.0750 g hydrated aluminum nitrate were dissolved into 72 mL of water. Then, 12 g of fumed silica was added and stirred until a homogeneous gel was formed. The gel was subjected to hydrothermal crystallization process at 200° C. for 2 days. The molar composition of the gel was 1 $SiO_2$: 0.08 TPABr: 0.0005 $Al_2O_3$: (0.5-2.0) $NH_4F$: 20 $H_2O$. The gel was washed with water and dried at 80° C. overnight. The template was removed by calcination at 750° C. for 6 h in air. The synthesized ZSM-5 zeolites with F/Si molar ratios of 0.5, 1.0, 1.6 and 2.0 are denoted by F-ZSM-5(A), F-ZSM-5(B), F-ZSM-5(C) and F-ZSM-5(D), respectively.

TABLE 1

Physico-chemical characterization of ZSM-5 with F/Si ratio of 0, 0.5, 1.0, 1.6, and 2.0.

| sample | F/Si molar ratio | Si/Al molar ratio | Surface area (m²/g) | $V_{total}$ (cm³/g) | NH₃-TPD (mmol/g) | | |
|---|---|---|---|---|---|---|---|
| | | | | | LT | HT | TA |
| ZSM-5(E) | 0 | 1049 | 354 | 0.17 | 0.0037 | 0.0070 | 0.0107 |
| ZSM-5(A) | 0.5 | 1182 | 374 | 0.17 | 0.0038 | 0.0073 | 0.0111 |
| ZSM-5(B) | 1.0 | 1198 | 379 | 0.19 | 0.0091 | 0.01 | 0.0191 |
| ZSM-5(C) | 1.6 | 1222 | 360 | 0.17 | 0.0098 | 0.0094 | 0.0192 |
| ZSM-5(D) | 2.0 | 1356 | 357 | 0.17 | 0.0095 | 0.0088 | 0.0183 |

LT = Low temperature;
HT = High temperature;
TA = Total Acidity

Example 2

ZSM-5 Synthesis without Fluoride by Hydrothermal Method

ZSM-5 with $Si/Al_2$ ratio of 2000 without $NH_4F$ was also synthesized using the following procedure. In a typical synthesis, 10.76 g sodium meta silicate and 0.28 g sodium hydroxide in 58.5 g of water was mixed in a beaker (Solution A). 2.36 g of tetrapropyl ammonium bromide in 86 g of $H_2O$ was mixed with 0.028 g hydrated aluminum sulfate. Then 1.55 g sulfuric acid was added (Solution B). In a separate beaker, 7 g of sodium hydroxide was dissolved in 137.5 g of water (Solution C) and Solution A followed by Solution B was added to this mixture. The obtained gel was aged for 24 h at constant stirring. The molar composition of the gel was 1 $SiO_2$: 0.1 $TPA^+$: 0.0005 $Al_2O_3$: 1.71 $Na_2O$: 178 $H_2O$. The mixture obtained was poured into a Teflon-sealed stainless steel bottle and heated to 150° C. for 72 h. The precipitate thus obtained was washed with alcohol, dried at 100° C. for 12 h, and calcined at 550° C. for 5 h in an air stream. Physically adsorbed and/or ion-exchanged sodium ions on the zeolite surface were removed and exchanged with $NH_4^+$ using a conventional ion exchange technique with a 10% $NH_4NO_3$ aqueous solution and calcined at 550° C. for 5 h in an air stream. The synthesized catalyst by this procedure is denoted as ZSM-5 (E).

Example 3

Catalytic Performance of Modified ZSM-5 Catalysts

The catalytic performance of the modified ZSM-5 catalysts was evaluated in a fixed-bed packed with 2 mL of the catalyst with a particle size of 0.5-1.0 mm diameter. The catalyst sample was pretreated in a nitrogen stream at 550° C. for 1 h and then a mixture of the 1-hexene (1.8 mL/h) and nitrogen (21 mL/min) (GHSV=900 $h^{-1}$) was passed through the catalyst bed at different temperature from 450 to 600° C. The products were analyzed by on-line GC equipped thermal conductivity detector (TCD) and a flame ionization detector (FID).

The results of catalytic performance in 1-hexene butene cracking using ZSM-5 catalysts are presented in Table 2. Catalyst D showed highest propylene as compared to other catalysts. Propylene yield was increased with reaction temperature from 450 to 600° C. as well as with increase in F/Si ratio. Time on stream study was carried out using Catalyst D is shown in FIG. 1. The results show that Catalyst C was stable for 50 hours of the 1-hexene stream. The amount of coke formation was found to be 0.77 wt % for catalyst D after 50 h of stream. For catalyst E, the coke formation was found to be 2.75 wt % within 5 hours of 1-hexene stream. This clearly indicates that the catalyst synthesized by fluoride method show excellent stability as compared without fluoride method.

Figure 3:
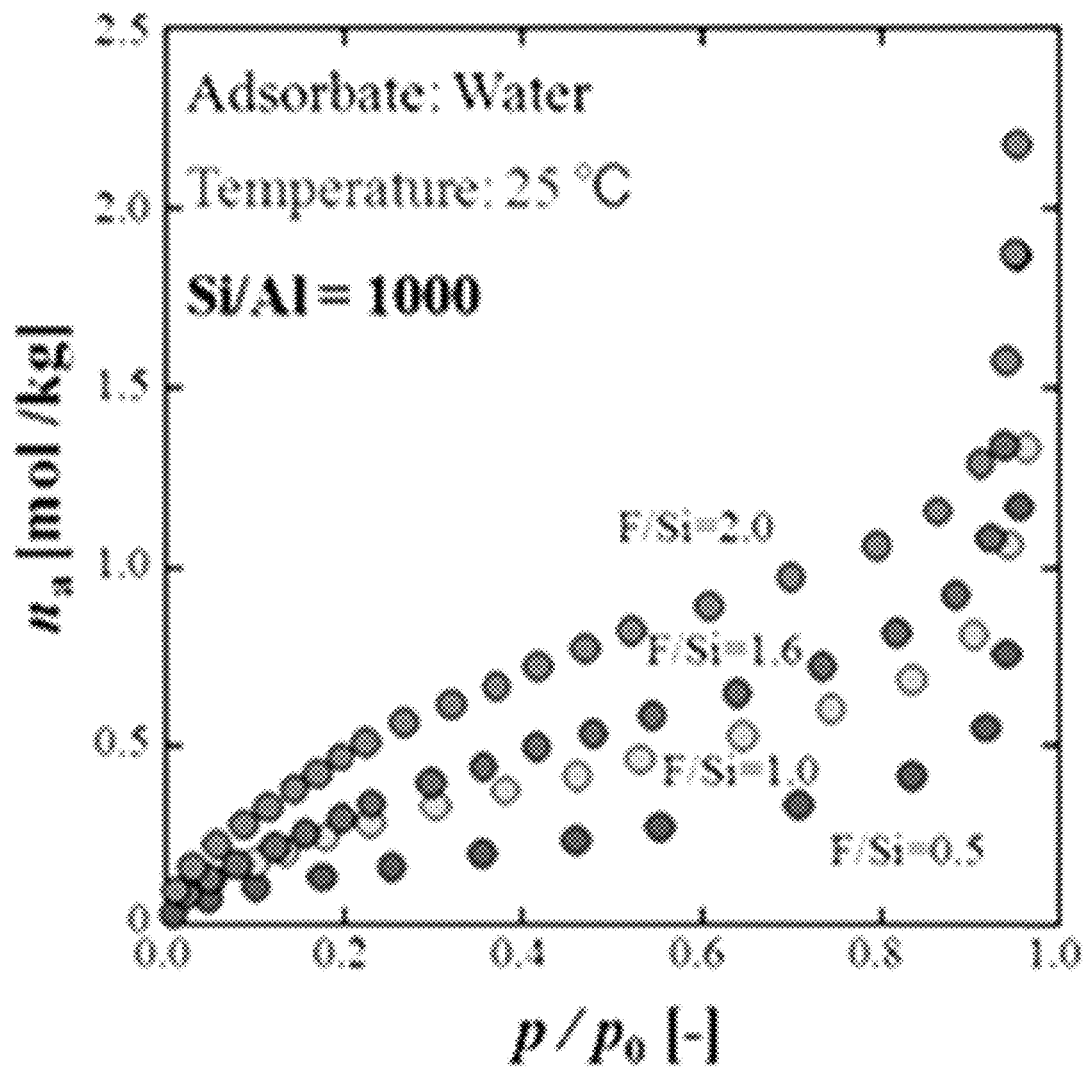
FIG. 3 shows water adsorption isotherms of fluoride functionalized zeolite catalysts.

The hydrophilic and hydrophobic properties of the modified ZSM-5 catalyst zeolite samples were measured using a water adsorption measurement, and the amount of water adsorbed is shown in FIG. 3. The water uptake behavior in FIG. 3 shows an increase in total water uptake capacity with an increase in the F/Si ratio. The amount of Al content in all the samples remained constant, indicating that the increase in water uptake is due to the presence of fluoride ions in ZSM-5.

The water adsorption measurements were carried out at 25° C. using a BELSORP MAX (BEL JAPAN Co. Ltd.) at water vapor saturated pressure (3.14 kPa at 25° C.). Before this measurement, the sample was degassed at 400° C. for 24 h.

The effect of fluoride ions on ZSM-5 catalyst synthesis and catalytic activity was studied. ZSM-5 was synthesized by a hydrothermal crystallization process using tetrapropyl ammonium bromide (TPABr) as a structure directing agent in a fluoride medium. The synthesized catalyst was used to perform a catalytic cracking reaction of 1-hexene in a fixed-bed reactor at 450-600° C. under atmospheric pressure. The effect of different ratios of fluoride ions was tested in the catalytic cracking of 1-hexene. The results revealed that ZSM-5 with F/Si ratio of 2 showed highest propylene selectivity of 72 wt % with 99% conversion of 1-hexene at 600° C. The synthesized ZSM-5 catalyst presented in this invention may be used in stand-alone units dedicated for the cracking of $C_4$-$C_6$ olefins, which are produced from FCC crackers or ethylene crackers. The effect of F/Si ratio was investigated by catalytic cracking of 1-hexene. The present invention produces a higher yield of propylene with different P/E ratio. The enhanced propylene selectivity is related to the amount of fluorine atom present in the zeolite framework, which may create a more hydrophilic environment in the catalyst. The hydrophilic nature of the catalyst with weak acid sites may be responsible for higher propylene selectivity. The catalyst lifetime studies showed that the catalyst was stable throughout 50 hours of exposure to a 1-hexene stream.

The invention claimed is:
1. A method for producing a fluoride functionalized zeolite catalyst, the method comprising:
   mixing a structure directing agent,
   an inorganic fluoride salt,
   an aluminum salt,
   a silicating agent, and

TABLE 2

Yield of light olefins (C-mol %) in cracking of 1-hexene using different catalysts at 1 bar, TOS = 1 hr, W/F = 0.125 h.

| | Reaction Temperature | | | | | | | | | | | |
|---|---|---|---|---|---|---|---|---|---|---|---|---|
| | 450° C. | | | 500° C. | | | 550° C. | | | 600° C. | | |
| Catalyst | C2= | C3= | C4= | C2= | C3= | C4= | C2= | C3= | C4= | C2= | C3= | C4= |
| ZSM-5(E) | 1.61 | 33.07 | 12.09 | 2.76 | 55.58 | 9.4 | 3.65 | 67.26 | 8.36 | 5.05 | 57.87 | 7.89 |
| ZSM-5(A) | 2.73 | 34.98 | 26.93 | 4.53 | 55.09 | 20.9 | 6 | 67.89 | 14.53 | 7.58 | 69.3 | 12.12 |
| ZSM-5(B) | 2.92 | 36.87 | 27.24 | 4.53 | 56.47 | 20.68 | 6.01 | 68.38 | 14.5 | 7.79 | 69.39 | 12.43 |
| ZSM-5(C) | 2.68 | 37.32 | 25.71 | 4.2 | 57.15 | 18.69 | 5.41 | 68.87 | 13.32 | 7.5 | 68.62 | 12.02 |
| ZSM-5(D) | 2.63 | 39.34 | 25.16 | 3.93 | 58.89 | 17.46 | 5.12 | 70.23 | 12.72 | 6.58 | 72.49 | 11.52 |

Example 4

Water Adsorption Isotherm of Modified ZSM-5 Catalysts with F/Si Ratios of 0.5, 1.0, 1.6, and 2.0.

water to form a gel, wherein the gel has a F to Si molar ratio of 1.5:1.0-2.1:1.0;

heating the gel at 180-250° C. for 12-72 h to produce a crystallized product; and calcining the crystallized product in air at 600-850° C. for 3-12 h to produce the fluoride functionalized zeolite catalyst, wherein the silicating agent is fumed silica, wherein the gel is formed from components consisting of the structure directing agent, the inorganic fluoride salt, the aluminum salt, the silicating agent, and water, wherein the fluoride functionalized zeolite catalyst has an average crystal size of 5-30 μm, wherein the fluoride functionalized zeolite catalyst has a Si to Al molar ratio of 1,000:1-1,200:1, and wherein the gel and the fluoride functionalized zeolite catalyst each comprises less than 0.005 wt % phosphorous and sodium relative to a respective total weight.

2. The method of claim 1, wherein the structure directing agent is a quaternary ammonium salt with a chemical formula $N(C_nH_{3n})_4^+X^-$, with X being a halide ion or a hydroxide, and n being an integer from 1 to 5.

3. The method of claim 2, wherein the structure directing agent is tetrapropylammonium bromide.

4. The method of claim 1, wherein the inorganic fluoride salt is ammonium fluoride.

5. The method of claim 1, wherein the aluminum salt is aluminum nitrate or aluminum sulfate.

6. The method of claim 1, wherein the fluoride functionalized zeolite catalyst has a total acidity of 0.017-0.020 mmol/g as defined by $NH_3$-TPD.

7. The method of claim 1, wherein the fluoride functionalized zeolite catalyst is a ZSM-5 type zeolite.

8. The method of claim 1, wherein the fluoride functionalized zeolite catalyst has a surface area of 330-400 $m^2$/g.

9. The method of claim 1, wherein the gel comprises the inorganic fluoride salt at a weight percentage of 0.6-1.0 wt %, relative to a total weight of the gel.

10. A fluoride functionalized zeolite catalyst, produced by the method of claim 1.

* * * * *